United States Patent [19]

Kozhemyakin et al.

[11]  4,212,949

[45]  Jul. 15, 1980

[54] APPARATUS FOR CULTIVATING MICROORGANISMS

[76] Inventors: Valentin G. Kozhemyakin, Leninsky prospekt, 85, korpus 6, kv. 45; Kalust A. Kaluniants, mikroraion Kapotnya, kvartal 4, 3, kv. 34; Lidia S. Losyakova, prospekt Mira, 89, kv. 181; Leonid I. Golger, Leningradsky prospekt, 43, korpus 9, kv. 31; Leonid F. Ivanov, ulitsa Marshala Birjuzova, 17, kv. 33; Raisa G. Kozlova, ulitsa Nagornaya, 34, korpus 43, kv. 14, all of Moscow, U.S.S.R.

[21] Appl. No.: 935,271

[22] Filed: Aug. 21, 1978

[51] Int. Cl.$^2$ .............................................. C12M 1/06
[52] U.S. Cl. ..................................... 435/315; 435/313
[58] Field of Search ............... 195/139, 140, 142, 143; 435/284, 304, 305, 306, 309, 313, 316, 315

[56]  References Cited

U.S. PATENT DOCUMENTS

| | | | |
|---|---|---|---|
| 3,216,908 | 11/1965 | Kratochvil | 195/143 |
| 3,575,813 | 4/1971 | Rothmayr | 195/142 X |
| 3,743,582 | 7/1973 | Kitai et al. | 195/142 X |
| 3,752,742 | 8/1973 | Jaekel et al. | 195/143 X |
| 3,801,468 | 4/1974 | Lumb et al. | 195/142 X |

*Primary Examiner*—R. B. Penland
*Attorney, Agent, or Firm*—Ladas, Parry, Von Gehr, Goldsmith & Deschamps

[57]  ABSTRACT

An apparatus for cultivating microorganisms on a granular medium comprises a vertical cylindrical vessel with a top port for charging the seeded granular medium and a bottom port for discharging the culture. The vessel is separated, heightwise, into sections by horizontal partitions, each section being provided with a tube for letting in an aerating flow of air and a tube for letting out the flow with metabolites. Each partition is composite and made up of partially overlapping circular sectors with perforation in the form of slots.

The sectors are provided with a means for shifting them so that when the medium is being charged into a section, all sectors form a solid plate, while, during discharge of the culture from the section, the sectors are shifted so that a free downward passage for the culture is provided.

The sector shifting means is located under the partition, relative to the medium, and provides for shifting of the sectors in a horizontal plane. Coaxially arranged with the section is a loosening means whose rake interacts with the culture to keep it loose.

12 Claims, 8 Drawing Figures

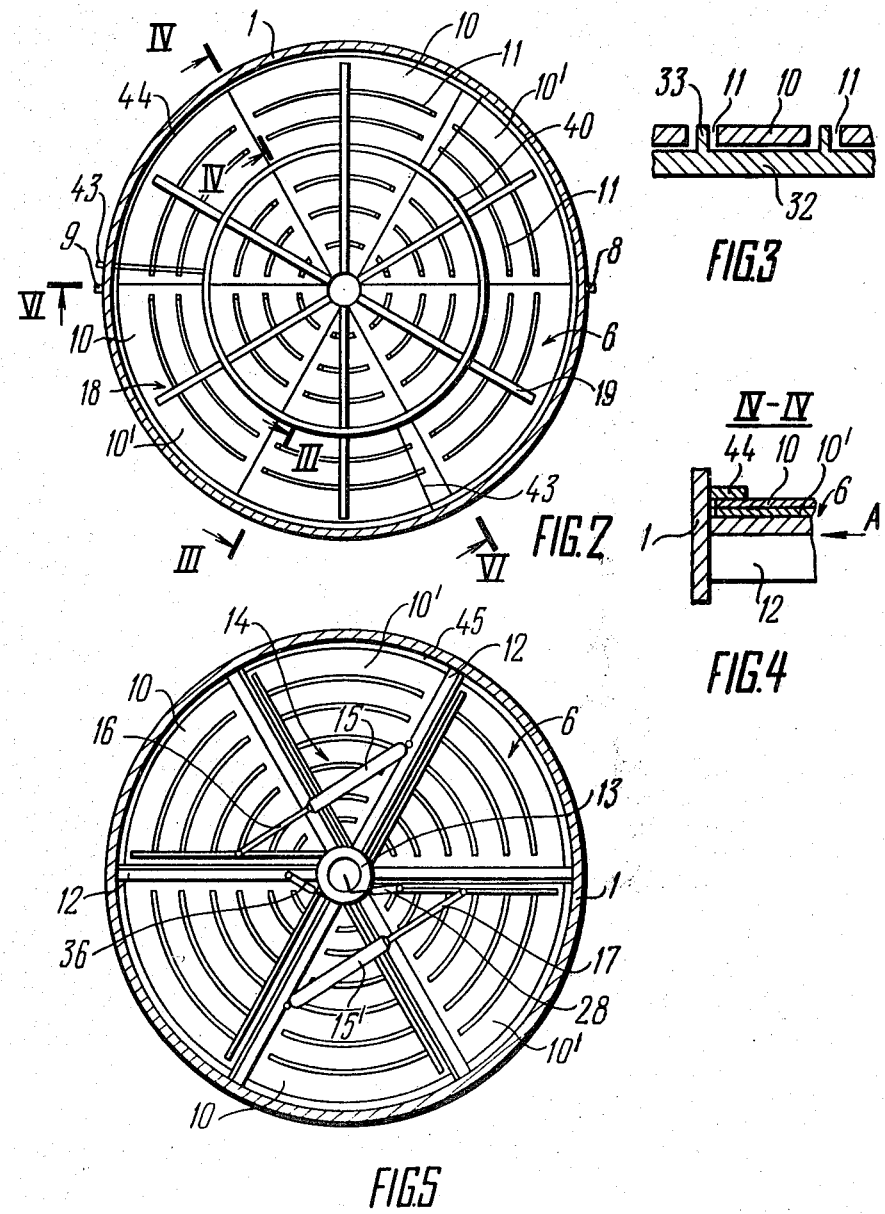

APPARATUS FOR CULTIVATING MICROORGANISMS

The present invention relates to the microbiological industry, and more particularly to apparatus for cultivating microorganisms.

The invention can most advantageously be used in cultivating microscopic fungi and bacteria in a porous bed of a granular medium having a moisture content of up to 70%. The process yields a culture containing residual particles of the growth medium with overlying colonies of microorganisms. The culture includes such ingredients as the biomass, metabolites, and biologically active substances, particularly, enzymes.

It is well known that cultivation of microorganisms in the bed of a medium consisting of, for example, sterilized and humidified wheat or rice bran, in the process of producing amylolytic enzymes, involves the use of such equipment as dishes or jars, rotary drums and stationary sectionalized apparatus.

The jars are filled with a medium for growing microorganisms, which forms a bed several centimeters thick, and placed on shelves in incubators. The latter are provided with air ducts associated with a fan. The aeration of the growing culture, which provides for the right temperature and humidity conditions during growth, as well as breathing, is effected by air supplied through the air duct and passing through the incubator chamber. In this case, the air flows parallel to the jar surfaces. The external heat and mass exchange in the incubator between the aerating flow of air and the growing culture does not permit the chamber to be charged with the medium above 15 to 20% of its capacity. Otherwise, the culture may be overheated and the enzymes may be inactivated, whereby the rate of biosynthesis goes down. In addition, such a process of cultivating microorganisms calls for relative sterility and manual labor.

With a view to increasing the yield of a culture per unit volume, apparatus in the form of rotary drums have been developed (cf. F. Webb, "Biochemical Technology and Microbiological Biosynthesis", "Meditsina" Publishers, Moscow, 1969 (in Russian). The drum has a port for charging a granular medium. Arranged coaxially with the drum, along its length is an air distributing device associated with a fan, ensuring aeration of the granular medium. As the drum revolves, the medium is agitated with the result that most of the medium is gradually exposed to the aerating flow, which improves the heat and mass exchange to some extent. However, the medium in the rotary drum is separated in a random fashion into pieces widely varying in size, whereby it is difficult to provide for uniform heat and mass exchange throughout the bed and, in addition, the integrity of the mycelium is affected by the mechanical action of the drum walls upon the culture. Practice has shown that the equipment cost per unit end product is too high.

Also known in the art is another apparatus with increased culture yield per unit volume, comprising a stationary vertical vessel separated heightwise by horizontal perforated partitions into sections (of. S. P. Koloskov, "Equipment of Enzyme Producing Industry", "Pischevaya promyshlennost" Publishers, Moscow, 1969 (in Russian). The partitions serve as supports for the medium bed and, at the same time, as air distributing elements. The vertical vessel has a top port for charging a granular medium and a bottom port for discharging the culture, as well as means for letting aeration air in and out. Arranged coaxially with the vessel is a vertical shaft provided with agitators in each section above the partitions. The partitions in the vessel are composite and made up of components adapted to rotate about the horizontal axis so that during charging and growth all components form a solid partition. At a particular point in time during the microorganism growth period, the partition components are positioned so that the section of the vessel provides free passage for the culture onto the lower partition. The partition components are rotated by a lever linked with the pivots of the components and with a drive. The lever is arranged outside the vessel.

The growing medium lies on a partition in a section and is blown with a sterile air flow, passing through the partition perforation which provides for convective heat and mass exchange throughout the medium, whereby the growing medium bed becomes higher. However, since the culture growth is accompanied by composite exothermal reactions of metabolism with simultaneous changes in the geometry of the medium's pore space due to microorganims cells appearing on the particles of the medium, stagnant zones occur in the granular medium bed. The appearance of these zones is due to local increases in the resistance to the air flow, which reduces the rate of removal of the metabolism energy. The released physiological heat raises the culture temperature to a maximum at which the growth rate is minimum. To ensure access of the aerating flow to the zones with overheating, impellers are used for agitation.

Such a design of an apparatus for cultivating microorganisms, however, disturbs the optimum growth conditions in all sections because the arrangement of impellers for each section on a common shaft results in that, as the medium is being agitated in a section where a stagnant zone is present, the culture is exposed to mechanical action even in sections without stagnant zones. The additional mechanical action adversely affects the integrity of the mycelium and reduces the rate of growth of the microorganisms.

To increase the rate of growth of microorganisms another culture growth apparatus has been provided (cf. USSR Inventor's Certificate No. 539,939; Cl. C 12 B 1/10; Dec. 25, 1976).

This apparatus comprises a vertical cylindrical vessel with a top port for charging a seeded granular medium and a bottom port for discharging the culture.

The vessel is separated, heightwise, into sections by horizontal partitions, each section being provided with tubes for letting a gas in and out. Each partition is composite and made up of perforated components adapted to be shifted so that, when the medium is being charged, all components form a solid plate, while during discharge of the culture, the horizontal section of the vessel is free for the downward passage of the culture. The partition components are shifted by levers each having one of its ends linked to the pivots of the components, while the other end of each lever is associated with an actuating cylinder arranged on the outer wall of the vessel. Each section in the vessel has agitating means made as a plurality of horizontal and vertical blades located on guides secured to a rotating shaft associated via a reducer with an individual drive arranged outside the section.

The partition components are made as segments each being cantilevered on the shaft.

An agitator in the form of an impeller is provided in the bottom part of the vessel.

A growth medium seeded with microorganism spores is charged through the top port into the upper section wherein the partition segments are in a horizontal position and form a solid bottom. The rotating agitator in this section levels the medium into a horizontal bed whose height reaches several tens of centimeters. After a certain period of time, the partition segments are turned by an appropriate lever to a vertical position, and the medium which was supported by the segments now drops on the partition of the lower section, in which the segments form a solid bottom at that moment. Then, the partition segments of the upper section are set to a horizontal position, and the section receives another portion of the medium. Thus, cyclic charging, growth and recharging of the medium into the remaining sections of the apparatus take place.

The necessary temperature and humidity conditions in the growing medium as well as breathing of the microorganisms are provided by an aerating flow of air. The air is introduced into a section through the inlet tube from under the partition, passes through the perforation, and traverses the medium bed taking up the heat released by the growing cells and ensuring $CO_2$ and $O_2$ gas exchange.

From the bottommost section the culture is discharged through the port with the aid of the impeller providing for the required looseness of the medium and delivered to subsequent processes.

In this prior art apparatus, the medium charge factor is increased up to 50%, nevertheless it suffers from a number of disadvantages. The cantilevered arrangement of the segments results in gaps between individual segments loaded with the medium, whereby the aeration of the culture becomes inadequate. From considerations of rigidity and strength, the width of each segment should not exceed ¼ to 1/5 of the vessel diameter. Besides, additional space is required to accommodate the partition segments as they are being shifted during transfer of the medium from one section to another, which space is not fully utilized and reduces the utilization factor of the vessel's volume.

In addition, the size of the perforation for passage of the air flow in the partition segments is selected such as to prevent growth medium particles from dropping therethrough. Thus, the diameter of holes in the segments must not exceed the average particle size. Reducing the hole diameter while retaining the required area for passage of the air flow creates serious difficulties in manufacture because drilling holes with a diameter less than the plate thickness raises the cost of manufacture and, at the same time, increases the resistance to air flow. However, even with minimum hole sizes, the perforation tends to be clogged by the cells of microorganisms whose size is in the micron range. Therefore, the holes being eventually clogged by tiny particles of the medium as it is being charged substantially reduces the aeration efficiency.

The agitator comprising a plurality of vertical and horizontal hollow blades permanently immersed in the medium bed affects the aerodynamic drag of the bed at the point of their installation. It is known that porosity at the wall-granular medium interface is always higher than in the rest of the mass, hence, the permeability is higher, too. Therefore, in the immediate proximity to the vertical blades, in the bed, the resistance to air flow is lower, whereas near the horizontal blades it is higher, which locally affects the aeration.

Finally, in the course of culture growth, the humidity of the growth medium decreases as part of the water is transferred into the cells and water vapors are entrained with the air flow. The decreased humidity adversely affects the rate of biosynthesis, and the introduction of an additional amount of water with the aerating flow is not effective enough because of the difficulties in controlling the complex process of mass transfer in a porous medium with microorganism cells.

Thus, the height of the growing bed, which, in the final analysis, determines the apparatus efficiency, is greater in such a design than in other apparatus. The use of agitators with individual drives in each section permits mitigating the intensity of the mechanical action on the microorganism cells.

However, the apparatus fill factor is reduced because of the space in the vessel, required for rotating the segments about the horizontal axis as the medium is being transferred from one section to another; in addition, increasing the height of fall of the culture is not desirable for this may damage the mycelium.

The perforation being clogged with microorganism particles and cells reduces the efficiency of aeration of the culture bed and causes shutdowns for washing and cleaning the partition segments.

The constant decrease in the culture humidity during the exponential and stationary growth phases results in a lower yield of the end product.

It is an object of the present invention to provide an apparatus for cultivating microorganisms, featuring high efficiency in terms of higher yield of the end product per unit volume, as well as ensuring optimum conditions for biosynthesis and integrity of the mycelium.

Another object of the invention is to render aeration more reliable.

Still another object of the invention is to provide conditions for directed biosynthesis.

Yet another object of the invention is to improve the sterility of the apparatus.

These and other objects are attained by that in an apparatus for cultivating microorganisms, comprising a vertical cylindrical vessel with a top port for charging a seeded granular medium and a bottom port for discharging the culture, said vessel being separated, heightwise, into sections by horizontal partitions, each section being provided with a tube for letting in an aerating flow of air and a tube for letting out the flow with metabolites, each partition being composite and made up of perforated components provided with a means for shifting them so that, when the medium is being charged into a section, all components form a solid plate, while, during discharge of the culture from the section, the components are shifted so that the horizontal section of the vessel becomes free for the downeard passage of the culture, according to the invention, in each section, the partition components are partially overlapping circular sectors with perforation in the form of slots, while the means for shifting them is located under the partition components, relative to the medium, and provides for shifting of the sectors in a horizontal plane, each section being provided with a loosening means arranged coaxially with the vessel and having a rake adapted to interact with the culture, thereby keeping it loose.

Such an embodiment of the partitions permits increasing the medium fill factor of the sections. In this case, no additional space is required to accommodate sectors as they are being shifted to provide passage for the medium. Therefore, the ratio of the end product mass to the apparatus volume increases by 25%.

In addition, the aeration conditions are improved due to the absence of gaps between the circular sectors of a partition when it is loaded with the medium bed.

The perforation being in the form of slots in circular sectors reduces energy losses in the aerating flow owing to the lower aerodynamic drag of the slots as compared to holes with the same passage area. The aerating flow passing through slots is more stable in the porous medium. The higher stability of the aerating flow in the medium bed minimizes the intensity of formation of stagnant zones in the growing bed, thereby providing more favorable conditions for biosynthesis. The slower formation of stagnant zones during cultivation permits reducing the intensity of agitation, hence, mechanical action. In this case, the mycelium is better protected against damage, which is another factor improving the biosynthesis conditions.

The arrangement of mechanisms actuating the sectors and the loosening means inside the vessel makes the use of gland or end seals unnecessary. Therefore, the penetration of infection into the apparatus from the environment is ruled out, and the sterility of growing microorganisms is improved.

The introduction of the means for maintaining the medium loose and, thereby, eliminating stagnant zones provides for a "softer" mechanical action on the culture, which keeps the mycelium intact and improves biosynthesis.

Preferably, each circular sector should be supported, in the area where it is overlapped by the adjacent sector, by a radial bearer having one of its ends rigidly secured to the inner wall of the vessel and the other end, to a central carrier ring concentrically arranged in the vessel.

The means for shifting the circular sectors should preferably comprise two actuating cylinders each being articulated to a respective radial bearer, whereas the rod of each cylinder is articulated to a respective circular sector.

It is expedient that the loosening means be provided with an actuating cylinder for its axial movement and an actuating cylinder for its rotation, the actuating cylinder for axial movement being located in the central carrier ring on sliding bearings, while the actuating cylinder for rotating the loosening means is articulated to the radial bearer and linked to the actuating cylinder for axial movement of the loosening means.

The axial movement of the loosening means being independent of its rotation enables mechanical action to be exerted only on that level of the culture bed where stagnant zones occur without affecting the other levels, whereby the integrity of the mycelium is maintained.

Each section should preferably be provided with a means for cleaning the slots, made in the form of a comb whose teeth are spaced apart to the same extent as the slots, the comb being located under the partition, relative to the medium, and linked with an actuating cylinder providing for movement of the teeth along the slots and articulated to the radial bearer.

Provision for the comb with teeth to clean the slots through which the air flow passes into the medium bed permits, if there is an actuating mechanism, cleaning in the course of cultivation, hence, ensuring efficient biosynthesis by maintaining reliable aeration.

Each section should preferably be provided with a collector having nozzles for feeding a fluid containing substances required for directed metabolism, hence, increasing the yield of the end product, the said collector being positioned above the loosening means and secured to the vessel walls. Feeding a fluid, e.g. water, into the medium bed through the nozzles compensates for humidity losses in the course of cultivation, while addition of various inductors and inhibitors affects the metabolism in the microorganism cells so as to increase the yield of the end product.

Other objects and advantages of the present invention will become more apparent from the following description of specific embodiments thereof with reference to the accompanying drawings.

FIG. 2 is a plan view along II—II of FIG. 1.

FIG. 3 is a section view along the line III—III of FIG. 2.

FIG. 4 is a section along IV—IV of FIG. 2.

FIG. 5 is a plan view along V—V of FIG. 1.

Figure 1:
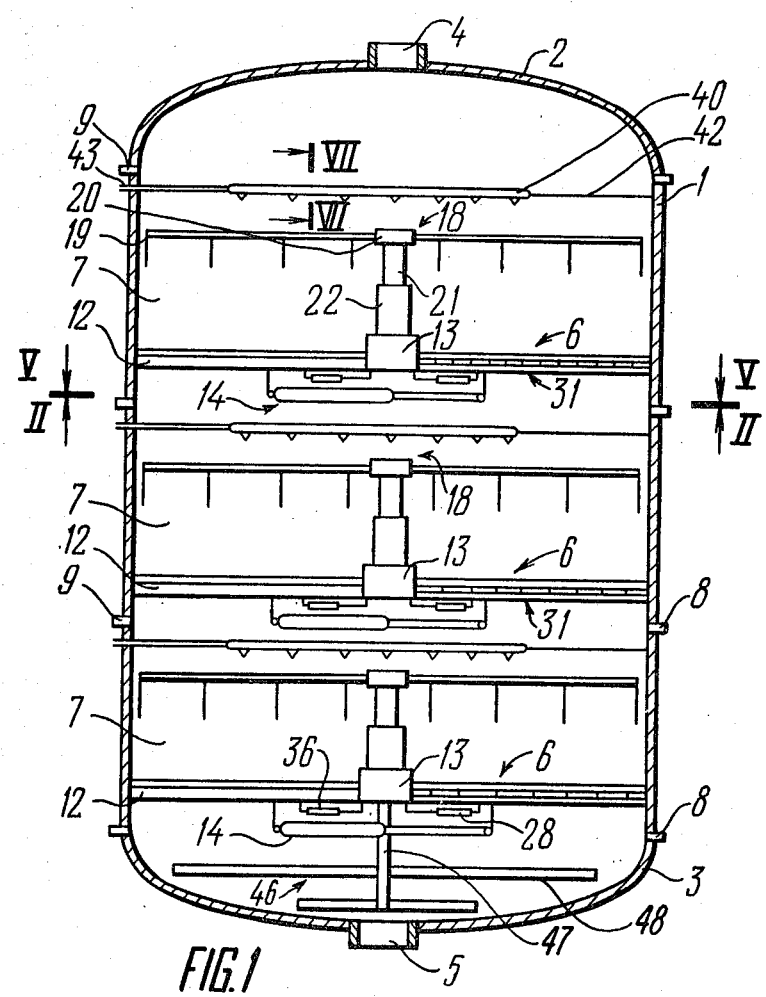
FIG. 1 is a vertical section of an apparatus according to the invention.

Referring now to FIG. 1, the apparatus for cultivating mocroorganisms, e.g. Aspergillus foefidus, comprises according to the invention, a vertical cylindrical vessel 1 covered on top and bottom with lids 2 and 3, respectively. The lid 2 is provided with a port 4 for charging a seeded granular medium, while the lid 3 has a port 5 for discharging the culture. The vessel 1 is separated, heightwise, by horizontal partions 6 into sections 7.

Figure 6:
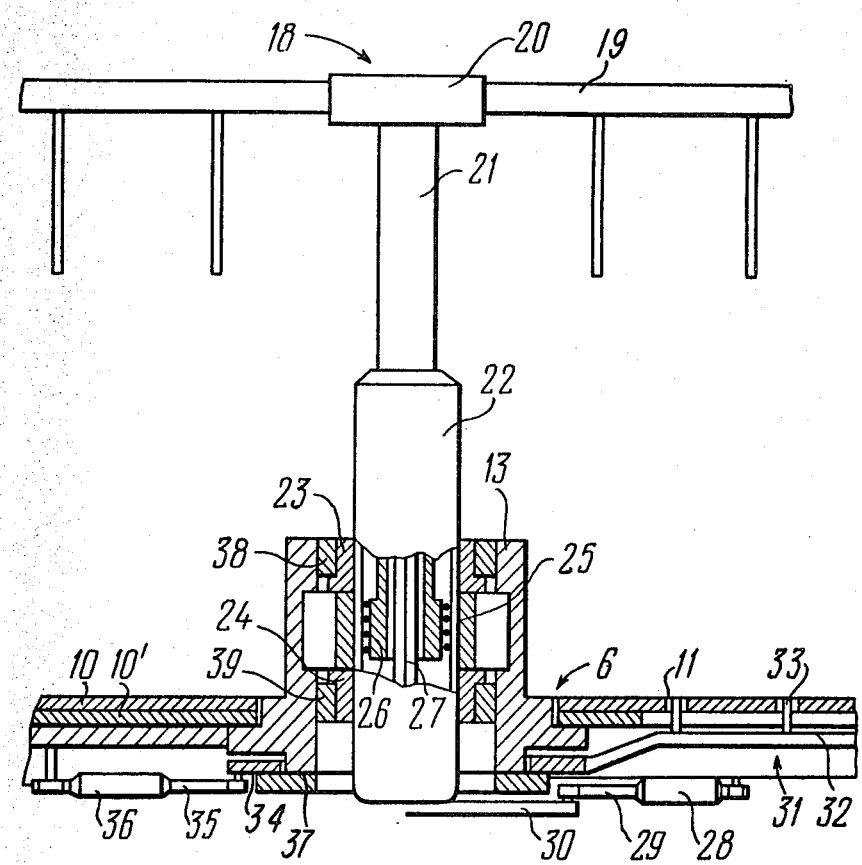
FIG. 6 is a partial, partially sectioned, view of a rake and partition component mechanism used in the apparatus of the invention.
Figure 7:
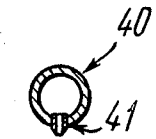
FIG. 7 is a section along the line VII—VII of FIG. 1.
Figure 8:
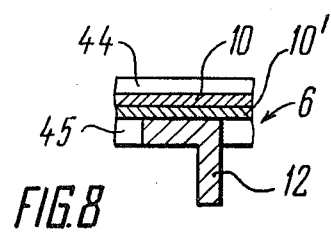
FIG. 8 is a section of a ring used in the partition components.

Each section 7 has a tube 8 for letting in the aerating flow of air and a tube 9 for letting out the air flow with metabolites. Each partition 6 (FIG. 2) is composite and made up of circular sectors 10 and 10'. The sectors 10 and 10' have perforation for passage of the aerating flow of air into the medium bed, in the form of slots 11 (FIG. 3). In addition, the sectors 10 and 10' partially overlap, which can easily be seen from FIG. 4. Each circular sector 10 and 10' is freely supported by a radial bearer 12 (FIG. 5) having one of its ends rigidly secured to the inner wall of the vessel 1, while the other end is rigidly secured to a central carrier ring 13 concentrically arranged in the vessel 1. The circular sectors 10 and 104' are provided with a means 14 for shifting them in a horizontal plane so that, when the medium is being charged into a section 7 (FIG. 1), all sectors 10 and 10' (FIG. 5) form a solid partition 6, while, during discharge of the culture from the section 7 (FIG. 1), the horizontal section of the vessel 1 becomes free for the downward passage of the culture. The means 14 comprises two actuating cylinders 15 and 15' (FIG. 5), the actuating cylinder 15 shifting the circular sectors 10 in a horizontal plane and actuating cylinder 15' shifting the circular sectors 10'. The actuating cylinder 15 is articulated to the radial bearer 12, and its rod 16 is articulated to the circular sectors 10. The actuating cylinder 15' is articulated to the radial bearer 12, and its rod 17 is articulated to the circular sectors 10'. The sectors 10 are interlinked to form a trefoil, just as the sectors 10'. Each section 7 (FIG. 1) is provided with a coaxially arranged loosening means 18 (FIG. 6) whose rake 19 is adapted to interact with the culture bed, keeping it loose. The rake 19 is associated, via a threaded bushing 20, with a rod 21 of an actuating cylinder 22 for its axial movement. The actuating cylinder 22 is located in the central carrier ring 13 on sliding bearings 23 and 24 separated by a distance piece 25 rigidly secured to the actuating cylinder 22. The rod 21 is made hollow with a squate cross section of the inner hole. A piston 26 has a hole through which passes a square bar 27 having one of its ends rigidly attached to the bottom of the cylinder 22, while the other end enters the rod 21, thereby ensuring that the latter does not rotate inside the cylinder. The loosening means 18 is provided with an actuating cylinder 28 for its rotation, articulated to the radial bearer 12, and its rod 29 is articulated to a lever 30 secured to the cylinder 22. Each section 7 (FIG. 1) is also provided with a means 31 for cleaning the slots 11 (FIG. 6), made in the form of a comb 32 whose teeth 33 are spaced apart to the same extent as the slots 11. The comb 32 is located under the partition 6, relative to the medium, and attached to a ring 34 located on the central carrier ring 13. The ring 34 is articulated to a rod 35 of an actuating cylinder 36 for moving the teeth 33 of the comb 32 along the slots 11, the cylinder 36 being articulated to the radial bearer 12. To prevent axial movement of the ring 34, a ring 37 is provided, rigidly secured to the central carrier ring 13. To prevent axial movement of the sliding bearings 23 and 24, provision is made for bushings 38 and 39, respectively. Each section 7 (FIG. 1) further comprises a distributor 40 with nozzles 41 (FIG. 7) for feeding a fluid containing substances necessary to intensify biosynthesis and increase the yield of the end product. The distributors 40 (FIG. 1) are arranged above the loosening means 18 and attached to the inner wall of the vessel 1 by means of arms 42. In addition, the distributors 40 have tubes 43 for letting in the fluid. Each partition 6 is prevented against axial movement along the vessel 1 by a ring 44 (FIG. 4) located above the partition 6 and a ring 45 (FIG. 8) located under the partition 6, relative to the medium. The rings 44 (FIG. 4) and 45 (FIG. 8) are secured to the inner wall of the vessel 1. Provided in the bottom portion of the vessel 1 (FIG. 1) is an impeller 46 comprising a shaft 47 secured on the actuating cylinder 22 and blades 48 for agitating the culture as it is being discharged through the port 5.

The cultivation process is effected by way of periodic sequential transfer of the medium from top to bottom through the sections 7 of the apparatus, the medium staying in each section for the same period of time.

Prior to charging, the vessel 1 should be sterilized, and the sections 7 are prepared for cultivation. To this end, the rods 16 and 17 (FIG. 5) of the cylinders 15 and 15' extend to the extreme outward position, and the forces transmitted to the points of articulation shift the circular sectors 10 and 10' apart so that the partition 6 spreads out forming a solid plate or bottom.

Through the port 4, a seeded growth medium having a temperature equal to that of cultivation during the lag phase is charged into the top section 7, falling on the partition 6. At the same time, fed into the medium is sterile water through the nozzles 41 (FIG. 7) of the distributor 40 to render the granular medium more humid.

Under the action of the rake 19 (FIG. 6) of the loosening means 18 positioned by the rod 21 at an appropriate height and rotating as a result of the reciprocating motion of the rod 29 of the cylinder 28, the charged medium is levelled, and a horizontal cylindrical bed 30 to 50 cm high is formed.

At the initial stage, adaptation of the microorganisms in the medium bed which is in the top section 7 takes place, followed by active growth. The cells absorb nutrients from the granular medium particles and gas phase of the pore space, and the process of metabolism is under way, providing for the microrganisms' vital activity. The process of growth of colonies is accompanied by breathing, hence, release of heat. Therefore, blown through the medium bed is sterile air fed through the tube 8 (FIG. 1), passing through the slots 11 (FIG. 3) of the circular sectors 10 and 10', and going out through the tube 9 (FIG. 1). The aeration at a certain temperature and moisture content of the air flow ensures external heat and mass exchange in the gas phase. $O_2$ is absorbed from the air flow, and $CO_2$ and $H_2O$ are introduced thereinto. As a result of the air being heated as it flows around the medium particles, heat is removed from the growing culture and the optimum temperature for biosynthesis is maintained.

Since the growth of colonies in the granular medium is accompanied by the microorganism cells filling the pore space, the permeability of the medium bed to air flow is affected, the medium becomes less loose because of the cohesion of particles, and the moisture content goes down. At the same time, the cells fill the slots 11 (FIG. 6) of the circular slots 10 and 10', which increases the resistance to air flow. These factors may result in stagnant zones in the medium bed, wherein the intensity of external heat and mass exchange as well as biosynthesis decreases. To maintain optimum conditions for cultivation, depending on the peculiarities of growth of a particular type of microorganisms, the medium is loosened by the rake 19, while the slots 11 are cleaned with the aid of the teeth 33 of the comb 32.

After a predetermined period of growth in the top section 7 (FIG. 1), the circular sectors 10 and 10' are shifted by the rods 16 and 17 (FIG. 5) retracting into the cylinders 15 and 15' so that the growing culture is free to pass into the next section 7 with additional feeding of the fluid containing agents promoting biosynthesis. In the next section, cultivation proceeds in the same manner as in the top section. In the latter, the circular sectors 10 and 10' (FIG. 2) are shifted apart and the charging process is repeated.

Repeated charging of the medium and transfer of the culture from one section to another provide for cyclic cultivation.

The growth process being over, the culture is discharged from the bottom section 7 through the port 5 with the aid of the blades 48 of the shaft 47 actuated by the cylinder 28. After discharge, the culture is delivered for subsequent processing.

The proposed apparatus for cultivating microorganisms features the following advantages:

(1) The highest possible medium fill factor of the apparatus. The sections contain no moving components requiring additional space for their movement.

(2) The perforation in the circular sectors being made in the form of slots along with provision being made for cleaning the slots ensure steady gas flow into the medium bed as the cleaning can be done at any time during cultivation. It is much easier to make slots of any width in the sectors than to drill holes with a diameter not exceeding the average particle size. Therefore, used for cultivation may be media with particle sizes ranging from 0.25 to 40 mm.

(3) The arrangement of mechanisms for moving components, made in the form of actuating cylinders, inside the vessel makes it possible to dispense with seals in the apparatus housing, which improves the sterility of cultivation.

(4) The provision for fluid collectors makes it possible to introduce promoters of biosynthesis of the end product.

While the preferred form of the present invention is shown and described by way of illustration, many modifications may occur to those skilled in the art, falling within the true spirit and scope of this invention.

What is claimed is:

1. An apparatus for cultivating microorganisms, comprising:
    a vertical cylindrical vessel;
    a top port for charging a seeded granular medium into said cylindrical vessel;
    a bottom port for discharging the culture from said cylindrical vessel;
    horizontal partitions separating said cylindrical vessel, into vertical sections,
    said horizontal partitions being made in the form of partially overlapping circular sectors and having perforation in the form of slots said sectors being moveable relative to each other in a horizontal plane;
    a means for shifting said components in a horizontal plane so that, when said medium is being charged into one of said sections, said components form a solid plate, while, during discharge of the culture from said section, a passage is provided for downward movement of the culture, said means being located under said partition;
    a plurality of loosening means provided in said vessel, each being located in one of said sections coaxially therewith;
    each being adapted to comb the contents of a section to keep them loose and means for introducing and letting out air from each compartment.

2. An apparatus as claimed in claim 1, comprising:
    a central carrier ring concentrically arranged in said vessel in each of said sections;
    radial bearers supporting said circular sectors in the area in which there is overlap of one sector by another; each radial bearer having one of its ends rigidly secured to the inner wall of said vessel, while the other end is rigidly secured to said central carrier ring.

3. An apparatus as claimed in claim 1, wherein said means for shifting said circular sectors comprises two actuating cylinders each comprising a rod and being articulated to a respective one of said radial bearers, while the rod of each said actuating cylinder is articulated to respective said circular sectors.

4. An apparatus as claimed in claim 1, comprising:
    an actuating cylinder for axial movement of each of said loosening means;
    sliding bearings supporting said actuating cylinder for axial movement of each of said loosening means, located in each of said central carrier rings;
    an actuating cylinder for rotation of each of said loosening means, articulated to one of said radial bearers and linked with said actuating cylinder for axial movement of one of said loosening means.

5. An apparatus as claimed in claim 1, comprising:
    a means for cleaning said slots, located in each section;
    a comb of said means for cleaning said slots, located under one of said partitions;
    the spacing of the teeth of said comb being the same as the spacing between said slots;
    an actuating cylinder for moving said teeth of said comb along said slots, linked with said comb and articulated to one of said radial bearers.

6. An apparatus as claimed in claim 1, comprising:
    a distributor in each of said sections, secured to the inner wall of said vessel and located above one of said loosening means;
    nozzles of said distributor, for feeding a fluid containing substances required to intensify biosynthesis and increase the yield of the culture.

7. An apparatus as claimed in claim 2, wherein said means for shifting said circular sectors comprises two actuating cylinders each being articulated to a respective one of said radial bearers, while the rod of each said actuating cylinder is articulated to respective said circular sectors.

8. An apparatus as claimed in claim 2, comprising:
    a means for cleaning said slots, located in each section;
    a comb of said means for cleaning said slots, located under one of said partitions;
    teeth of said comb, spaced apart to the same extent as said slots;
    an actuating cylinder for moving said teeth of said comb along said slots, linked with said comb and articulated to one of said radial bearers.

9. An apparatus as claimed in claim 2, comprising:
    a distributor in each of said sections, secured to the inner wall of said vessel and located above one of said loosening means;
    nozzles of said distributor, for feeding a fluid containing substances required to intensify biosynthesis and increase the yield of the culture.

10. An apparatus as claimed in claim 7, comprising:
    a means for cleaning said slots, located in each section;
    a comb of said means for cleaning said slots, located under one of said partitions;
    teeth of said comb, spaced apart to "the same extent" as said slots;
    an actuating cylinder for moving said teeth of said comb along said slots, linked with said comb and articulated to one of said radial bearers.

11. An apparatus as claimed in claim 7, comprising:
    a distributor in each of said sections, secured to the inner wall of said vessel and located above one of said loosening means;
    nozzles of said distributor, for feeding a fluid containing substances required to intensify biosynthesis and increase the yield of the culture.

12. An apparatus as claimed in claim 10, comprising:
    a distributor in each of said sections, secured to the inner wall of said vessel and located above one of said loosening means;
    nozzles of said distributor, for feeding a fluid containing substances required to intensify biosynthesis and increase the yield of the culture.

* * * * *